United States Patent
Nicou et al.

(10) Patent No.: US 11,213,471 B2
(45) Date of Patent: Jan. 4, 2022

(54) COMPOSITION FOR DYEING THE HAIR, COMPRISING AN OXIDATION BASE, A 2-AMINO-5-ETHYLPHENOL COUPLER AND A FATTY SUBSTANCE

(71) Applicant: L'OREAL, Paris (FR)

(72) Inventors: Valérie Nicou, Saint-Ouen (FR); Aziz Fadli, Aulnay-sous-Bois (FR); Frédéric Legrand, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/063,719

(22) PCT Filed: Dec. 20, 2016

(86) PCT No.: PCT/EP2016/082001
§ 371 (c)(1),
(2) Date: Jun. 19, 2018

(87) PCT Pub. No.: WO2017/108841
PCT Pub. Date: Jun. 29, 2017

(65) Prior Publication Data
US 2020/0345604 A1 Nov. 5, 2020

(30) Foreign Application Priority Data
Dec. 21, 2015 (FR) ...................... 1562909

(51) Int. Cl.
| A61Q 5/10 | (2006.01) |
| A61K 8/41 | (2006.01) |
| A61K 8/22 | (2006.01) |
| A61K 8/31 | (2006.01) |
| A61K 8/49 | (2006.01) |
| A61K 8/92 | (2006.01) |

(52) U.S. Cl.
CPC ............ *A61K 8/415* (2013.01); *A61K 8/22* (2013.01); *A61K 8/31* (2013.01); *A61K 8/494* (2013.01); *A61K 8/92* (2013.01); *A61Q 5/10* (2013.01); *A61K 2800/4324* (2013.01); *A61K 2800/882* (2013.01)

(58) Field of Classification Search
CPC ............ A61Q 5/10; A61K 2800/4324; A61K 2800/882; A61K 8/31; A61K 8/92; A61K 8/22; A61K 8/415
USPC ..................................................... 8/405, 421
See application file for complete search history.

(56) References Cited

U.S. PATENT DOCUMENTS

| 4,003,699 A | 1/1977 | Rose et al. |
| 4,137,180 A | 1/1979 | Naik et al. |
| RE30,199 E | 1/1980 | Rose et al. |
| 4,840,639 A | 6/1989 | Husemeyer et al. |
| 4,874,554 A | 10/1989 | Lange et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,099,593 A | 8/2000 | Terranova et al. |
| 6,284,003 B1 | 9/2001 | Rose et al. |
| 6,730,789 B1 | 5/2004 | Birault et al. |
| 9,125,834 B2 | 9/2015 | Couroux et al. |
| 9,220,671 B2 | 12/2015 | Ascione et al. |
| 9,370,477 B2 | 6/2016 | Allard et al. |
| 2005/0011016 A1* | 1/2005 | Pasquier ................ A61K 8/415 8/405 |
| 2005/0166335 A1 | 8/2005 | Vidal et al. |
| 2007/0067926 A1* | 3/2007 | Schmitt .................... A61Q 5/10 8/405 |
| 2007/0136959 A1 | 6/2007 | Fadli |
| 2007/0143935 A1 | 6/2007 | Fadli et al. |
| 2009/0282622 A1 | 11/2009 | Dahlgren et al. |
| 2012/0180230 A1* | 7/2012 | Schmenger ............. A61Q 5/08 8/405 |
| 2012/0210519 A1 | 8/2012 | Lim et al. |
| 2013/0312203 A1* | 11/2013 | Allard .................. C07D 471/04 8/409 |
| 2015/0139925 A1 | 5/2015 | Kamikawa et al. |
| 2015/0283053 A1 | 10/2015 | Odman Schmid et al. |

FOREIGN PATENT DOCUMENTS

| CA | 2615230 A1 | 4/2008 |
| CN | 101312707 A | 11/2008 |
| DE | 2359399 A1 | 6/1975 |
| DE | 3843892 A1 | 6/1990 |
| DE | 4133957 A1 | 4/1993 |

(Continued)

OTHER PUBLICATIONS

Final Office Action for co-pending U.S. Appl. No. 16/062,282, dated Oct. 22, 2019.
International Search Report for counterpart Application No. PCT/EP2016/082000, dated Mar. 28, 2017.
International Search Report for counterpart Application No. PCT/EP2016/082011, dated May 15, 2017.

(Continued)

*Primary Examiner* — Eisa B Elhilo
(74) *Attorney, Agent, or Firm* — The Marbury Law Group, PLLC

(57) ABSTRACT

The present invention relates to a composition for dyeing keratin fibres, comprising an oxidation base, a 2-amino-5-ethylphenol coupler and at least 20% by weight of fatty substance relative to the total weight of the composition.

The invention also relates to a process for dyeing keratin fibres using this composition.

Finally, the invention relates to the use of such a composition for dyeing keratin fibres, and in particular the hair.

20 Claims, No Drawings

(56) References Cited

FOREIGN PATENT DOCUMENTS

| | | | |
|---|---|---|---|
| DE | 19543988 | A1 | 5/1997 |
| DE | 202005014897 | U1 | 11/2005 |
| EP | 0007537 | A1 | 2/1980 |
| EP | 0770375 | A1 | 5/1997 |
| EP | 1550656 | A1 | 7/2005 |
| EP | 1792606 | A1 | 6/2007 |
| EP | 1792903 | A1 | 6/2007 |
| FR | 2733749 | A1 | 11/1996 |
| FR | 2750048 | A1 | 12/1997 |
| FR | 2801308 | A1 | 5/2001 |
| FR | 2886136 | A1 | 12/2006 |
| FR | 2893027 | A1 | 5/2007 |
| FR | 2988594 | A1 | 10/2013 |
| GB | 1026978 | A | 4/1966 |
| GB | 1153196 | A | 5/1969 |
| JP | 02-019576 | A | 1/1990 |
| JP | 05-163124 | A | 6/1993 |
| JP | 2015-512367 | A | 4/2015 |
| WO | 80/00214 | A1 | 2/1980 |
| WO | 94/08969 | A1 | 4/1994 |
| WO | 94/08970 | A1 | 4/1994 |
| WO | 96/15765 | A1 | 5/1996 |
| WO | 01/35917 | A1 | 5/2001 |
| WO | 2004041225 | A1 | 5/2004 |
| WO | 2007034410 | A1 | 3/2007 |
| WO | 2010/133640 | A2 | 11/2010 |
| WO | 2012/080289 | A2 | 6/2012 |
| WO | 2013/152956 | A1 | 10/2013 |
| WO | 2017/108840 | A1 | 6/2017 |
| WO | 2017/108847 | A1 | 6/2017 |

OTHER PUBLICATIONS

Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
International Search Report from International Searching Authority for International Application No. PCT/EP2016/082001, dated Mar. 28, 2017, 4 pages.
Non-Final Office Action for copending U.S. Appl. No. 16/062,282, dated Feb. 28, 2020.
Non-Final Office Action for co-pending U.S. Appl. No. 16/062,282, dated Jun. 12, 2019.
Notice of Reasons for Refusal for counterpart JP Application No. 2018-532092, dated May 7, 2019 with Translation.
Notice of Reasons for Refusal for counterpart JP Application No. 2018-532093, dated Jul. 1, 2019 with Translation.
Notice of Reasons for Refusal for counterpart JP Application No. 2018-532094, dated May 7, 2019 with Translation.
Translation of Japanese Office Action for counterpart Application No. 2019-145549, dated Oct. 19, 2020.
Final Office Action for copending U.S. Appl. No. 16/062,282, dated Jul. 30, 2020.
Translation of Chinese Office Action for counterpart Application No. 201680074384.9, dated Jul. 24, 2020.
Translated Chinese Office Action for counterpart Application No. 201680074386.8, dated Jun. 28, 2020.
Translated Chinese Office Action for counterpart Application No. 201680074381.5, dated Aug. 10, 2020.
Non-Final Office Action for copending U.S. Appl. No. 16/062,282, dated May 28, 2021.
Non-Final Office Action for copending U.S. Appl. No. 16/062,207, dated Jul. 7, 2021.
Final Office Action for copending U.S. Appl. No. 16/062,282, dated Nov. 5, 2021.

* cited by examiner

COMPOSITION FOR DYEING THE HAIR, COMPRISING AN OXIDATION BASE, A 2-AMINO-5-ETHYLPHENOL COUPLER AND A FATTY SUBSTANCE

CROSS REFERENCE TO RELATED APPLICATIONS

This is a national stage application of PCT/EP2016/082001, filed internationally on Dec. 20, 2016, which claims priority to French Application No. 1562909, filed on Dec. 21, 2015, both of which are incorporated by reference herein in their entireties.

The present invention relates to a composition for dyeing keratin fibres, comprising an oxidation base, a 2-amino-5-ethylphenol coupler and at least 20% by weight of fatty substance relative to the total weight of the composition.

The invention also relates to a process for dyeing keratin fibres using this composition.

Finally, the invention relates to the use of such a composition for dyeing keratin fibres, and in particular the hair.

Many people have sought for a long time to modify the colour of their hair and in particular to mask their grey hair.

It is known practice to dye keratin fibres, in particular human keratin fibres such as the hair, to obtain "permanent" colourations with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds which, when combined with oxidizing products, may give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained.

However, the use of these dye compositions may have a certain number of drawbacks.

Specifically, after application to keratin fibres, the dyeing power obtained may not be entirely satisfactory, or may even be weak, and lead to a restricted range of colours.

The colourations may also not be sufficiently persistent with respect to external agents such as light, shampoo or perspiration, and may also be too selective, i.e. the difference in colouration is too great along the same keratin fibre that is differently sensitized between its end and its root.

By way of example, the 2-amino-5-ethylphenol coupler is known from document DE202005014897. In said document, it is combined with another m-aminophenol coupler and oxidation bases for dyeing the hair in a varied manner. According to said document, it is possible, with such a combination, to obtain uniform colourations from the root to the end of the hair.

These combinations do not however make it possible to obtain an entirely satisfactory colouration. This is because they did not make it possible to provide good coverage of the keratin fibres, and in particular of depigmented keratin fibres, such as grey hair. Moreover, their dyeing capacity often proves to be limited.

Thus, there is a real need to provide a composition for dyeing keratin fibres, in particular human keratin fibres such as the hair, which does not have the drawbacks mentioned above, i.e. which is capable of leading to a strong colouration with good coverage of grey hair while at the same time having good fastness.

These aims and others are achieved by the present invention, one subject of which is thus a composition for dyeing keratin fibres, comprising:
(a) one or more oxidation bases,
(b) at least one 2-amino-5-ethylphenol coupler or an addition salt or solvate thereof, and
(c) at least one liquid fatty substance different from salified fatty acids, in a total amount of greater than or equal to 20% by weight relative to the total weight of the composition.

Another subject of the present invention is a process for dyeing keratin fibres in which the composition according to the invention is applied to said fibres.

The invention also relates to the use of said composition for dyeing keratin fibres, and in particular the hair.

This composition gives particularly good coverage of depigmented keratin fibres such as grey hair.

The composition according to the invention makes it possible to produce particularly intense and sparingly selective colourations, i.e. colourations that are uniform along the length of the fibre.

Moreover, the colourations obtained by means of the composition according to the invention withstand well the various attacking factors to which the hair may be subjected, such as light, bad weather, washing and perspiration.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expressions "at least one" and "at least" used in this description are equivalent to the expressions "one or more" and "greater than or equal" respectively.

(a) The 2-amino-5-ethylphenol Coupler

The composition according to the invention comprises one or more 2-amino-5-ethylphenol couplers, in free-form, or addition salts thereof or solvates thereof.

The addition salts are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, aqueous ammonia, amines or alkanolamines.

Moreover, the solvates more particularly represent the hydrates of the 2-amino-5-ethylphenol coupler and/or the combination of the 2-amino-5-ethylphenol coupler with a linear or branched $C_1$ to $C_4$ alcohol such as methanol, ethanol, isopropanol or n-propanol. Preferably, the solvates are hydrates.

The total amount of the 2-amino-5-ethylphenol coupler or an addition salt or solvate thereof, present in the composition according to the invention, can range from 0.0001% to 20% by weight, preferably from 0.005% to 10% by weight, and more preferentially from 0.01% to 6% by weight, relative to the total weight of the composition.

(b) Liquid Fatty Substance

The composition according to the invention also comprises one or more fatty substances different from salified fatty acids wherein at least 20% of the fatty substances are liquid. Preferably, the fatty substance(s) is (are) liquid at ambient temperature (25° C.) and at atmospheric pressure ($1.013 \times 10^5$ Pa).

The term "fatty substance" is intended to mean an organic compound that is insoluble in water at ambient temperature (25° C.) and at atmospheric pressure ($1.013 \times 10^5$ Pa) (solubility of less than 5% by weight, and preferably less than 1% by weight, even more preferentially less than 0.1% by weight). They bear in their structure at least one hydrocarbon-based chain comprising at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "oil" is intended to mean a "fatty substance" that is liquid at ambient temperature (25° C.) and at atmospheric pressure ($1.013 \times 10^5$ Pa).

The term "non-silicone fatty substance" is intended to mean a fatty substance not containing any Si—O bonds and the term "silicone fatty substance" is intended to mean a fatty substance containing at least one Si—O bond.

The fatty substances used in the composition according to the invention are different from salified fatty acids, i.e. they can be present in the composition in the form of free fatty acids.

In other words, the fatty substances of the invention do not contain any salified carboxylic acid groups (—C(O)O—). Particularly, the fatty substances of the invention are neither polyoxyalkylenated nor polyglycerolated.

Preferably, the fatty substances are different from non-salified fatty acids.

Preferably, the composition according to the invention comprises one or more fatty substances that are liquid at ambient temperature and atmospheric pressure ($1.013 \times 10^5$ Pa), different from salified fatty acids.

More particularly, the liquid fatty substances according to the invention are chosen from $C_6$ to $C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid fatty acid and/or fatty alcohol esters other than triglycerides, and silicone oils, and mixtures thereof.

It is recalled that the fatty alcohols and esters more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$ to $C_{16}$ liquid hydrocarbons, they are linear, branched or optionally cyclic, and are preferably alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly, polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil, and mixtures thereof.

The liquid fatty alcohols that are suitable for use in the invention are more particularly chosen from linear or branched, saturated or unsaturated, preferably unsaturated or branched, alcohols comprising from 6 to 30 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols other than the triglycerides mentioned above, mention may be made in particular of esters of saturated or unsaturated, linear $C_1$ to $C_{26}$ or branched $C_3$ to $C_{26}$ aliphatic monoacids or polyacids and of saturated or unsaturated, linear $C_1$ to $C_{26}$ or branched $C_3$ to $C_{26}$ aliphatic monoalcohols or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononate; octyldodecyl erucate; oleyl erucate; ethyl palmitate, isopropyl palmitate, 2-ethylhexyl palmitate, 2-octyldecyl palmitate, alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of $C_4$ to $C_{22}$ dicarboxylic or tricarboxylic acids and of $C_1$ to $C_{22}$ alcohols and esters of mono-, di- or tricarboxylic acids and of $C_2$ to $C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononate; and polyethylene glycol distearates, and mixtures thereof.

The composition may also comprise, as fatty ester, sugar esters and diesters of $C_6$ to $C_{30}$ and preferably $C_{12}$ to $C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$ to $C_{30}$ and preferably $C_{12}$ to $C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof such as, in particular, the mixed esters oleo-palmitate, oleo-stearate and palmito-stearate.

More particularly, use is made of monoesters and diesters and in particular sucrose, glucose or methylglucose mono- or dioleates, stearates, behenates, oleopalmitates, linoleates, linolenates and oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicone oils that may be used in the composition according to the present invention may be volatile or non-volatile, cyclic, linear or branched silicone oils, which are unmodified or modified with organic groups, and preferably have a viscosity from $5 \times 10^{-6}$ to $2.5$ $m^2/s$ at $25°$ C., and preferably $1 \times 10^{-6}$ to $1$ $m^2/s$.

Preferably, the silicone oils are chosen from polydialkylsiloxanes, in particular polydimethylsiloxanes (PDMS), and liquid polyorganosiloxanes comprising at least one aryl group.

These silicone oils can also be organomodified. The organomodified silicone oils that may be used in accordance with the invention are preferably liquid silicones as defined above and comprising in their structure one or more organofunctional groups attached via a hydrocarbon-based group, chosen, for example, from amine groups and alkoxy groups.

Organopolysiloxanes are defined in greater detail in Walter Noll's *Chemistry and Technology of Silicones* (1968), Academic Press. They may be volatile or non-volatile.

When they are volatile, the silicone oils are more particularly chosen from those with a boiling point of between 60° C. and 260° C., and even more particularly from:

(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ $m^2/s$ at $25°$ C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile polydialkylsiloxanes are preferably used.

These silicone oils are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 $mm^2/s$;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

The organomodified silicones that may be used in accordance with the invention are silicones as defined above and comprising in their structure one or more organofunctional groups attached via a hydrocarbon-based group.

As regards the liquid polyorganosiloxanes comprising at least one aryl group, they may in particular be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ $m^2/s$ at $25°$ C.

Among these polyalkylarylsiloxanes, examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may be made of polyorganosiloxanes comprising:

substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are, in particular, $C_1$ to $C_4$ aminoalkyl groups; alkoxy groups, hydroxyl groups.

The liquid fatty substance(s) is (are) preferentially chosen from liquid hydrocarbons containing more than 16 carbon atoms, plant oils, liquid fatty alcohols and liquid fatty esters, silicone oils and mixtures thereof.

Preferentially, the liquid fatty substance(s) is (are) chosen from liquid hydrocarbons comprising more than 16 carbon atoms, in particular liquid petroleum jelly.

Preferably, the total amount of fatty substance(s) present in the composition according to the invention is greater than or equal to 30% by weight, and more preferentially greater than or equal to 35% by weight, relative to the total weight of the composition.

More preferentially, the total amount of fatty substance(s) present in the composition according to the invention ranges from 30% to 80% by weight, and preferably from 30% to 70% by weight, relative to the total weight of the composition.

Even more preferentially, the total amount of liquid fatty substance(s) present in the composition according to the invention is greater than or equal to 30% by weight, and more preferentially greater than or equal to 35% by weight, relative to the total weight of the composition.

Even better still, the total amount of liquid fatty substance(s) present in the composition according to the invention ranges from 30% to 80% by weight, and preferably from 30% to 70% by weight, relative to the total weight of the composition.

Oxidation Bases

The composition according to the invention may also comprise one or more oxidation bases.

Among the oxidation bases that are of use for the invention, mention may be made of para-phenylenediamines, bis(phenyl)alkylenediamines, para-aminophenols, bis-para-aminophenols, ortho-aminophenols and heterocyclic bases, the addition salts thereof, and solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-γ-hydroxypropyl-para-phenylenediamine, 2-fluoro-para-phenylenediamine, 2-isopropyl-para-phenylenediamine, N-(β-hydroxpropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid and solvates thereof.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof with an acid and solvates thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid and solvates thereof.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid and solvates thereof.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts.

Among the 3-aminopyrazolo[1,5-a]pyridine bases, it will in particular be preferred to use 2[(3-aminopyrazolo[1,5-a]pyridin-2-yl)oxy]ethanol, and/or 4-(3-aminopyrazolo[1,5-a]pyridin-2-yl)-1,1-dimethylpiperazin-1-ium chloride and/or the corresponding addition salts or solvates thereof.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyhamino-1-methylpyrazole, and the corresponding addition salts. Use may also be made of 4,5-diamino-1-(β-methoxyethyl)pyrazole.

Among the pyrazole derivatives, a 4,5-diaminopyrazole will preferably be used and even more preferentially 4,5-diamino-1-(β-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Among the heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or 2[(3-aminopyrazolo[1,5-a]pyridin-2-yl)oxy]ethanol and/or 4-(3-aminopyrazolo[1,5-a]pyridin-2-yl)-1,1-dimethylpiperazin-1-ium chloride and/or the corresponding salts or solvates thereof.

In one variant of the invention, the composition comprises one or more oxidation bases chosen from heterocyclic bases, preferably chosen from 4,5-diamino-1-(β-hydroxyethyl)pyrazole and/or 2,3-diamino-6,7-dihydro-1H,5H-pyrazolo[1,2-a]pyrazol-1-one and/or 2[(3-aminopyrazolo[1,5-a]pyridin-2-yl)oxy]ethanol and/or 4-(3-aminopyrazolo[1,5-a]pyridin-2-yl)-1,1-dimethylpiperazin-1-ium chloride and/or the salts or solvates thereof.

The addition salts of the oxidation bases present in the composition according to the invention are chosen in particular from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, aqueous ammonia, amines or alkanolamines.

Moreover, the solvates of the oxidation bases more particularly represent the hydrates of the oxidation bases and/or the combination of the oxidation bases with a linear or branched $C_1$ to $C_4$ alcohol such as methanol, ethanol, isopropanol or n-propanol. Preferably, the solvates are hydrates.

The total amount of oxidation base(s) present in the composition according to the invention can range from 0.0001% to 20% by weight, preferably from 0.005% to 10% by weight and more preferentially from 0.01% to 6% by weight, relative to the total weight of the composition.

The composition of the invention may contain other couplers different from the 2-amino-5-ethylphenol coupler according to the invention. Among these couplers, mention may in particular be made of meta-phenylenediamines, meta-aminophenols other than 2-amino-5-ethylphenol, meta-diphenols, naphthalene couplers, heterocyclic couplers, the addition salts thereof, solvates thereof and mixtures thereof.

Among the couplers that can be used in the composition according to the invention, mention may particularly be made of 6-hydroxybenzomorpholine, 1,3-dihydroxybenzene, 2-methyl-1,3-dihydroxybenzene, 1-hydroxy-3-aminobenzene, 2-methyl-5-hydroxyethylaminophenol, 2,4-diaminophenoxyethanol, 4-amino-2-hydroxytoluene, 2,4-dichloro-3-aminophenol, 5-amino-4-chloro-o-cresol, 5-amino-6-chloro-o-cresol, 4-chloro-1,3-dihydroxybenzene, 1-β-hydroxyethyloxy-2,4-diaminobenzene, 2-amino 4-(β-hydroxyethylamino)-1-methoxybenzene, 1,3-bis(2,4-diaminophenoxy) propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxpaphthalene, 2,7-naphthalenediol, 1-acetoxy-2-methylnaphthalene, 6-hydroxyindole, 4-hydroxyindole, 4-hydroxy N-methylindole, 2-amino 3-hydroxypyridine, 3,5-diamino-2,6-dimethoxypyridine, 2,6-dihydroxy-3-4-dimethylpyridine, 3-amino-2-methylamino-6-methoxypyridine, 6-hydroxybenzomorpholine, 1-N-(β-hydroxyethyl)amino-3,4-methylenedioxybenzene, 2,6-bis(β- hydroxyethylamino)toluene, 3-methyl-1-phenyl 5-pyrazolone, the addition salts thereof with an acid and the solvates thereof.

The addition salts, the hydrates and the solvates of the couplers present in the composition according to the invention are as described above for the coupler that is of use in the invention.

Preferably, the additional coupler(s) present in the composition according to the invention is (are) chosen from 6-hydroxybenzomorpholine, 2,4-diaminophenoxyethanol, 1,3-dihydroxybenzene, 1-hydroxy-3-aminobenzene, 2-methyl-5-hydroxyethylaminophenol, 2-methyl-1,3-dihydroxybenzene, 2-amino 3-hydroxypyridine, the addition salts thereof, solvates thereof and mixtures thereof.

When it (they) is (are) present, the total amount of additional coupler(s) in the composition according to the invention can range from 0.0001% to 20%, preferably from 0.005% to 10% by weight and more preferentially from 0.01% to 6% by weight, relative to the total weight of the composition.

Preferably, the total amount of coupler(s) in the composition according to the invention ranges from 0.0001% to 20% by weight, preferably from 0.005% to 10% by weight and better still from 0.01% to 6% by weight, relative to the total weight of the composition.

Surfactants

The composition according to the invention may optionally also comprise one or more surfactants.

The surfactant(s) that may be used in the composition according to the invention may be chosen from non-ionic, cationic, anionic and amphoteric or zwitterionic surfactants.

The composition according to the invention may comprise one or more non-ionic surfactants.

The non-ionic surfactants that may be used are described, for example, in the *Handbook of Surfactants* by M. R. Porter, published by Blackie & Son (Glasgow and London), 1991, pp. 116-178.

Examples of non-ionic surfactants that may be mentioned include the following non-ionic surfactants:
  oxyalkylenated ($C_8$-$C_{24}$)alkylphenols;
  saturated or unsaturated, linear or branched, oxyalkylenated or glycerolated $C_8$ to $C_{40}$ alcohols, comprising one or two fatty chains;
  saturated or unsaturated, linear or branched, oxyalkylenated $C_8$ to $C_{30}$ fatty acid amides;
  esters of saturated or unsaturated, linear or branched, $C_8$ to $C_{30}$ acids and of polyethylene glycols;
  preferably oxyethylenated esters of saturated or unsaturated, linear or branched, $C_8$ to $C_{30}$ acids and of sorbitol;
  esters of fatty acids and of sucrose;
  ($C_8$-$C_{30}$)alkyl(poly)glucosides, ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl (poly)glucoside esters;
  saturated or unsaturated oxyethylenated plant oils;
  condensates of ethylene oxide and/or of propylene oxide;
  N—($C_8$-$C_{30}$)alkylglucamine and N—($C_8$-$C_{30}$)acylmethylglucamine derivatives;
  aldobionamides;
  amine oxides;
  oxyethylenated and/or oxypropylenated silicones;
  and mixtures thereof.

The oxyalkylene units are more particularly oxyethylene or oxypropylene units, or their combination, preferably oxyethylene units.

The number of moles of ethylene oxide and/or propylene oxide preferably ranges from 1 to 250, more particularly from 2 to 100 and better still from 2 to 50; the number of moles of glycerol ranges in particular from 1 to 50 and better still from 1 to 10.

Advantageously, the non-ionic surfactants according to the invention do not comprise any oxypropylene units.

By way of example of glycerolated non-ionic surfactants, use is preferably made of monoglycerolated or polyglycerolated $C_8$ to $C_{40}$ alcohols comprising from 1 to 50 mol of glycerol, preferably from 1 to 10 mol of glycerol.

As examples of compounds of this type, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

Among the glycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The non-ionic surfactant(s) that may be used in the composition according to the invention are preferentially chosen from:
  oxyethylenated $C_8$ to $C_{40}$ alcohols comprising from 1 to 100 mol of ethylene oxide, preferably from 2 to 50 and more particularly from 2 to 40 mol of ethylene oxide and comprising one or two fatty chains;
  saturated or unsaturated oxyethylenated plant oils comprising from 1 to 100 and preferably from 2 to 50 mol of ethylene oxide;
  ($C_8$-$C_{30}$)alkyl(poly)glucosides, which are optionally oxyalkylenated (0 to 10 OE) and comprising 1 to 15 glucose units;
  monoglycerolated or polyglycerolated $C_8$ to $C_{40}$ alcohols, comprising from 1 to 50 mol of glycerol and preferably from 1 to 10 mol of glycerol;
  saturated or unsaturated, linear or branched, oxyalkylenated $C_8$ to $C_{30}$ fatty acid amides;
  esters of saturated or unsaturated, linear or branched, $C_8$ to $C_{30}$ acids and of polyethylene glycols;
  and mixtures thereof.

The composition according to the invention may comprise one or more cationic surfactants.

The term "cationic surfactant" is intended to mean a surfactant that is positively charged when it is contained in the composition according to the invention. This surfactant may bear one or more positive permanent charges or may contain one or more cationizable functions in the composition according to the invention.

The cationic surfactant(s) is (are) preferably chosen from primary, secondary or tertiary fatty amines, which are optionally polyoxyalkylenated, or salts thereof, and quaternary ammonium salts, and mixtures thereof.

The fatty amines generally comprise at least one $C_8$ to $C_{30}$ hydrocarbon-based chain.

Mention may in particular be made, as quaternary ammonium salts, for example, of:
  quaternary ammonium salts such as tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salts, the stearamidopropyltrimethylammonium salts, the stearamidopropyldimethylcetearylammonium salts, or the stearamidopropyldimethyl(myristyl acetate)ammonium salts sold under the name Ceraphyl® 70 by the company Van Dyk. It is preferred in particular to use the chloride salts of these compounds;

- quaternary ammonium salts of imidazoline, for example sold under the name Rewoquat® W 75 by the company Rewo;
- di- or triquaternary ammonium salts, for example, Finquat CT-P available from the company Finetex (Quaternium 89), and Finquat CT, available from the company Finetex (Quaternium 75);
- quaternary ammonium salts containing at least one ester function, such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

Such compounds are sold, for example, under the names Dehyquart® by the company Henkel, Stepanquat® by the company Stepan, Noxamium® by the company CECA or Rewoquat® WE 18 by the company Rewo-Witco.

Use may also be made of the ammonium salts containing at least one ester function that are described in U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts comprising at least one ester function comprise two ester functions.

Among the quaternary ammonium salts containing at least one ester function, which may be used, it is preferred to use dipalmitoylethylhydroxyethyl-methylammonium salts.

The composition according to the invention may comprise one or more anionic surfactants.

The term "anionic surfactant" is intended to mean a surfactant comprising, as ionic or ionizable groups, only anionic groups. These anionic groups are preferably chosen from the groups —COOH, —COO$^-$, —SO$_3$H, —SO$^{3-}$, —OSO$_3$H, —OSO$^{3-}$, —PO$_2$H$_2$, —PO$_2$H$^-$, —PO$_2^{2-}$, —P(OH)$_2$, =P(O)OH, —P(OH)O$^-$, =P(O)O$^-$, =POH, =PO$^-$, the anionic parts comprising a cationic counterion such as an alkali metal, an alkaline-earth metal or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglucoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids, and the corresponding non-salified forms of all these compounds, the alkyl and acyl groups of all these compounds comprising from 6 to 40 carbon atoms and the aryl group denoting a phenyl group.

These compounds may be oxyethylenated and then preferably comprise from 1 to 50 ethylene oxide units.

The salts of $C_6$ to $C_{24}$ alkyl monoesters of polyglucoside-polycarboxylic acids may be chosen from $C_6$ to $C_{24}$ alkyl polyglucoside-citrates, $C_6$ to $C_{24}$ alkyl polyglucoside-tartrates and $C_6$ to $C_{24}$ alkyl polyglucoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts and in particular of sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferred to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The composition according to the invention may comprise one or more amphoteric or zwitterionic surfactants.

In particular, the amphoteric or zwitterionic surfactant(s), which is (are) preferably non-silicone, which may be used in the composition according to the present invention may in particular be derivatives of optionally quaternized, secondary or tertiary aliphatic amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

Mention may in particular be made of ($C_8$-$C_{20}$)alkyl betaines, ($C_8$-$C_{20}$)alkyl sulfobetaines, ($C_8$-$C_{20}$)alkylamido ($C_3$-$C_8$)alkyl betaines and ($C_8$-$C_{20}$)alkylamido($C_6$-$C_8$)alkyl sulfobetaines.

Among the optionally quaternized, secondary or tertiary aliphatic amine derivatives that can be used, mention may be made of the compounds classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Mention may be made of the compound classified in the CTFA dictionary under the name sodium diethylaminopropyl cocoaspartamide and sold by the company Chimex under the name Chimexane HB.

These compounds may be used alone or as mixtures.

Among the amphoteric or zwitterionic surfactants mentioned above, use is preferably made of ($C_8$-$C_{20}$)alkylbetaines such as cocobetaine, ($C_8$-$C_{20}$)alkylamido($C_3$-$C_8$) alkylbetaines such as cocamidopropylbetaine, and mixtures thereof, and the compounds of formula (VIII) such as the sodium salt of diethylaminopropyl laurylaminosuccinamate (INCI name: sodium diethylaminopropyl cocoaspartamide).

Preferably, the composition according to the invention comprises one or more surfactants. More preferentially, the composition according to the invention comprises one or more surfactants chosen from non-ionic, anionic or amphoteric surfactants.

Particularly preferably, the composition according to the invention comprises one or more non-ionic surfactants. The total amount of surfactant(s), present in the composition according to the invention, can range from 0.1% to 25% by weight, and preferably from 0.5% to 20% by weight, relative to the total weight of the composition.

Alkaline Agents

The composition according to the invention may optionally also comprise one or more alkaline agents.

Preferably, the dye composition comprises one or more organic or mineral alkaline agents.

The mineral alkaline agent(s) is (are) preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) is (are) preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chain comprising more than ten carbon atoms.

The organic alkaline agent(s) is (are) chosen, for example, from alkanolamines, oxyethylenated and/or oxypropylenated ethylenediamines, amino acids and the compounds of formula (IX) below:

(IX)

in which formula (IX) W is a divalent $C_1$ to $C_6$ alkylene radical optionally substituted with one or more hydroxyl groups or a $C_1$ to $C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$ to $C_6$ alkyl, $C_1$ to $C_6$ hydroxyalkyl or $C_1$ to $C_6$ aminoalkyl radical.

Examples of amines of formula (IX) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are, for example, histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made in particular of carnosine, anserine and balenine.

The organic amine may also be chosen from compounds comprising a guanidine function. As amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention is (are) chosen from aqueous ammonia, alkanolamines and amino acids in neutral or ionic form, in particular basic amino acids.

More preferentially, the alkaline agent(s) present in the composition according to the invention, is (are) chosen from aqueous ammonia, alkanolamines, and mixtures thereof. According to one particular embodiment, the alkaline agent is an organic agent, preferably an alkanolamine. When the alkaline agent is an alkanolamine, it is chosen from monoethanolamine.

The total quantity of alkaline agent(s) present in the composition according to the invention may range from 0.01% to 30% by weight, and preferably from 0.1% to 20% by weight, relative to the total weight of the composition.

The composition according to the invention may optionally also comprise one or more organic solvents.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The organic solvent(s) may be present in an amount ranging from 0.01% to 30% by weight, preferably ranging from 2% to 25% by weight, relative to the total weight of the composition.

The composition according to the invention may also optionally comprise one or more additives, different from the compounds of the invention and among which mention may be made of cationic, anionic, non-ionic or amphoteric polymers or mixtures thereof, antidandruff agents, antiseborrhoeic agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, in particular polymeric thickeners, opacifiers or nacreous agents, antioxidants, hydroxy acids, fragrances, preservatives, pigments and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above adjuvants may generally be present in an amount, for each of them, of between 0 and 20% by weight relative to the total weight of the ready-to-use composition.

Chemical Oxidizing Agent

According to one particular embodiment of the invention, the composition according to the invention comprises at least one chemical oxidizing agent.

The expression "chemical oxidizing agent" is intended to mean an oxidizing agent other than atmospheric oxygen.

In particular, the chemical oxidizing agent(s) is (are) chosen, for example, from hydrogen peroxide, urea peroxide, alkali metal bromates, peroxygenated salts, such as for example persulfates or perborates, peracids and precursors thereof and alkali metal or alkaline-earth metal percarbonates. Advantageously, the oxidizing agent is hydrogen peroxide.

The chemical oxidizing agent(s) may be present in a content ranging from 0.5% to 20%, better still from 1% to 15% by weight, relative to the total weight of the composition.

When the composition of the invention contains at least one alkaline agent and at least one oxidizing agent, the composition is then ready to use. It can be applied to the hair so as to allow the keratin fibres to be dyed.

When the composition of the invention contains the alkaline agent and the oxidizing agent, it preferably contains at least 20% of fatty substances, preferably liquid fatty substances, preferably at least 30% by weight, relative to the total weight of the composition. Preferably, this ready-to-use composition contains between 30% and 55% of fatty substances, preferably liquid fatty substances, preferably between 35% and 50%.

Process of the Invention

Another subject of the invention is a process for dyeing human keratin fibres, in particular the hair, comprising the application to the keratin fibres of the composition according to the invention.

According to one preferred embodiment, the composition contains at least one alkaline agent and at least one oxidizing agent. The composition is then applied to the keratin fibres and left on for approximately 3 to 50 minutes, preferably approximately 5 to 40 minutes, then there follows a step of rinsing, washing with a shampoo, again rinsing and, finally, drying.

If the composition of the invention is not mixed before application with the alkaline agent and the oxidizing agent, the various compositions can be applied sequentially, in any order, with or without intermediate rinsing.

According to another embodiment, the composition according to the invention results from the mixing of at least two compositions:

a dye composition comprising at least one oxidation base, at least one 2-amino-5-ethylphenol coupler or a salt or solvate thereof, and at least one alkaline agent, and an oxidizing composition comprising one or more chemical oxidizing agents; any one of the compositions also contains one or more fatty substances, which are preferably liquid at ambient temperature and atmospheric pressure, different from salified fatty acids;

such that the total amount of fatty substances, preferably liquid fatty substances, is greater than or equal to 30% by weight relative to the total weight of the composition resulting from the mixing of the above two compositions, preferably between 30% and 55%, preferably 35% to 50%.

According to this embodiment, at least one of the compositions is an aqueous composition.

The term "aqueous composition" is intended to mean a composition in which the amount of water is greater than or equal to 5% by weight relative to the weight of the composition. Preferably, the amount of water is greater than or equal to 10% by weight.

Preferably, the dye composition comprises one or more fatty substances, which are preferably liquid at ambient temperature and atmospheric pressure, different from salified fatty acids, in a total amount of greater than or equal to 30% by weight, more preferentially greater than or equal to 40% by weight, better still greater than or equal to 50% by weight and even better still greater than or equal to 60% by weight, relative to the weight of the dye composition.

More preferentially, the dye composition comprises one or more fatty substances, which are preferably liquid at ambient temperature and atmospheric pressure, different from salified fatty acids, in a total amount of greater than or equal to 30% by weight relative to the weight of the dye composition, and the oxidizing composition comprises one or more fatty substances, which are preferably liquid at ambient temperature and atmospheric pressure, different from salified fatty acids, in a total amount of greater than or equal to 10% by weight relative to the weight of the oxidizing composition, preferably between 15% and 25%.

The dye composition (A) and the oxidizing composition (B) are preferably mixed in a weight ratio (A)/(B) ranging from 0.2 to 10 and more preferentially from 0.5 to 2.

In accordance with this embodiment, the dyeing process thus consists in applying to the keratin fibres the dye composition resulting from the mixing of the dye composition (A) and the oxidizing composition (B) mentioned above.

Multi-Compartment Device:

Another subject of the invention is a multi-compartment device, preferably comprising at least two compartments, for dyeing keratin fibres, at least one first compartment containing the dye composition (A) according to the invention and at least one second compartment containing the oxidizing composition (B) as described above.

Finally, the present invention relates to the use of a composition as described above, for dyeing keratin fibres, and in particular the hair.

According to the present application, the term "keratin fibres" denotes human keratin fibres and in particular the hair.

The examples that follow serve to illustrate the invention without, however, being limiting in nature.

EXAMPLES

In the examples that follow, all the amounts are given as percentages by weight relative to the total weight of the composition. Unless otherwise indicated, the amounts are indicated in Active Material (unless otherwise mentioned).

Example 1 a) Dye Compositions

The following dye compositions, A1 to A3, according to the invention were prepared from the ingredients of which the contents are indicated in the table below.

| Chemical name | A1 | A2 | A3 |
|---|---|---|---|
| POWDERED SODIUM METABISULFITE | 0.45 | 0.45 | 0.45 |
| PURE MONOETHANOLAMINE | 5.13 | 5.16 | 5.15 |
| ETHYLENEDIAMINE TETRAACETIC ACID | 0.2 | 0.2 | 0.2 |
| 1-METHYL-2-HYDROXY-4-BETA-HYDROXYETHYLAMINOBENZENE | 0.033 | 0.033 | 0.04 |
| 1-BETA-HYDROXYETHYLOXY-2,4-DIAMINOBENZENE DIHYDROCHLORIDE | 0.048 | 0.038 | |
| 2-METHYL-1,3-DIHYDROXYBENZENE (2-METHYLRESORCINOL) | 0.27 | 0.33 | 0.33 |
| 2-AMINO-3-HYDROXYPYRIDINE | | | 0.1 |
| 2,3-DIAMINO-6,7-DIHYDRO-1H,5H-PYRAZOLO[1,2-A]PYRAZOL-1-ONE DIMETHANESULFONATE | 0.485 | 0.39 | 0.49 |
| 3-(2,5-DIAMINOPHENYL)PROPAN-1-OL HYDROCHLORIDE | 0.6 | 0.72 | 0.9 |
| MINERAL OIL | 60 | 60 | 60 |
| FRAGRANCE | 0.95 | 0.95 | 0.95 |
| POLYQUATERNIUM-67 (CATIONIC LAURYL MODIFIED CELLULOSE ETHER) | 0.19 | 0.19 | 0.19 |
| 2-AMINO-5-ETHYLPHENOL HCL | 0.23 | 0.28 | 0.33 |
| WATER | Qs 100 | qs 100 | qs 100 |
| OXYETHYLENATED STEARYL ALCOHOL (2 OE) | 1.13 | 1.13 | 1.13 |
| OXYETHYLENATED STEARYL ALCOHOL (20 OE) | 3.88 | 3.88 | 3.88 |
| ALKYL (C8/C10 50/50) POLYGLUCOSIDE (2) | 2.4 | 2.4 | 2.4 |
| OXYETHYLENATED SORBITAN MONOLAURATE (4 OE) | 2.4 | 2.4 | 2.4 |
| VITAMIN C: ASCORBIC ACID | 0.25 | 0.25 | 0.25 | b) Oxidizing Compositions

The following oxidizing composition, B1, was prepared from the ingredients of which the contents are indicated in the table below.

| | Composition B1 |
|---|---|
| Diethylenetriaminepentaacetic acid, pentasodium salt | 0.06 |
| Hydrogen peroxide | 6 |
| Disodium tin hexahydroxide | 0.04 |
| Tetrasodium pyrophosphate decahydrate | 0.03 |
| Liquid petroleum jelly | 20 |
| Poly[(dimethyliminio)-1,3-propanediyl (dimethyliminio)-1,6-hexanediyl dichloride] as an aqueous solution at 60% | 0.15 |
| Polydimethyldiallylammonium chloride | 0.2 |
| Glycerol | 0.5 |
| Cetylstearyl alcohol (30/70: $C_{16}/C_{18}$) | 6 |
| Oxyethylenated stearyl alcohol (20 OE) | 5 |
| Vitamin D: DL-alpha-tocopherol | 0.1 |
| Phosphoric acid | qs pH = 2.2 ± 0.2 |
| Water | qs 100 |

Procedure

The dye compositions A1 to A3 are mixed respectively with the oxidizing composition B1 in a 1:1 ratio.

The mixtures thus obtained, A1+B1, A2+B1 and A3+B1, are applied to locks of natural hair containing 90% grey hairs.

After a leave-on time of 35 minutes at ambient temperature, the locks are rinsed with clear water, then washed with a shampoo. Finally, the locks are dried.

The colour of the locks was evaluated visually.

Powerful colourations are obtained in the shades indicated below.

| Formula | Formula Name |
|---|---|
| A1 + B1 | Light blonde shade |
| A2 + B1 | Dark blonde shade |
| A3 + B1 | Golden mahogany dark blonde |

Example 2

The following compositions were prepared:

| | A4 (invention) | A5 (comparative) |
|---|---|---|
| 2-Amino-5-ethylphenol · HCl | $6.3 \times 10^{-3}$ mol | — |
| Resorcinol | — | $6.3 \times 10^{-3}$ mol |
| 2,4-Diaminophenoxyethanol · HCl | 0.144 | 0.144 |
| m-Aminophenol | 0.112 | 0.112 |
| 2,5-Toluenediamine | 0.729 | 0.729 |

|  | A4 (invention) | A5 (comparative) |
|---|---|---|
| Monoethanolamine | 4.34 | 4.34 |
| Sodium metabisulfite | 0.22 | 0.22 |
| Glycerol | 5 | 5 |
| Deceth-5 | 1.08 | 1.08 |
| Oleth-10 | 1 | 1 |
| Oleth-20 | 4 | 4 |
| C20-22 alcohols | 4.6 | 4.6 |
| Cetyl palmitate | 2 | 2 |
| Ceteareth-60 myristyl glycol | 0.01 | 0.01 |
| Mineral oil | 60 | 60 |
| Carbomer | 0.1 | 0.1 |
| EDTA | 0.2 | 0.2 |
| Ascorbic acid | 0.12 | 0.12 |
| Water | Qs 100 | Qs 100 |

The dye compositions A4 to A5 are mixed respectively with the oxidizing composition B1 in a 1:1 ratio.

The mixtures thus obtained, A4+B1 and A5+B1, are applied to locks of natural hair containing 90% grey hairs.

After a leave-on time of 35 minutes at ambient temperature, the locks are rinsed with clear water, then washed with a shampoo. Finally, the locks are dried.

The locks are then subjected to a test of 12 shampooing operations in order to evaluate the fastness with respect to washing.

The colorimetric measurements are performed before the test, and then after the test, using a Minolta CM2600D spectrocolorimeter (illuminant D65, angle 10°, specular components included) in the CIE Lab system.

The fastness with respect to washing is represented by the colour difference ΔE between the dyed locks before and after the 12-shampoo test according to the equation:

$$\Delta E = \sqrt{(L^*-L_0^*)^2+(a^*-a_0^*)^2+(b^*-b_0^*)^2}$$

where $L^*$, $a^*$ and $b^*$ represent the values measured on the locks of dyed hair before the test, and $L_0^*$, $a_0^*$ and $b_0^*$ represent the values measured on locks of dyed hair after the test.

The lower the value of ΔE, the better the fastness with respect to washing.

|  | L* | a* | b* | ΔE |
|---|---|---|---|---|
| A4 + B1 (invention) before test | 19.14 | 0.22 | 0.29 | 2.4 |
| A4 + B1 (invention) after test | 21.33 | 0.65 | 1.25 |  |
| A5 + B1 (comparative) before test | 19.15 | 0.22 | 0.67 | 4.5 |
| A5 + B1 (comparative) after test | 22.64 | 0.76 | 3.51 |  |

The mixture obtained with composition A4 according to the invention has a lower ΔE value, and thus a better fastness with respect to washing, compared with the mixture obtained with composition A5.

Example 3

Dye Compositions (in g % of Active Material Unless Otherwise Mentioned)

|  | A6 (invention) | A7 (comparative) |
|---|---|---|
| 2-Amino-5-ethylphenol · HCl | $2.5 \times 10^{-3}$ mol | $3.125 \cdot 10^{-3}$ mol |
| 2,5-Toluenediamine | $2.5 \times 10^{-3}$ mol | $3.125 \cdot 10^{-3}$ mol |
| Monoethanolamine | 4.96 | 1.2 |
| Sodium metabisulfite | 0.22 | 0.71 |
| Glycerol | 5 | — |
| Deceth-5 | 1.08 | — |
| Oleth-10 | 1 | — |
| Oleth-20 | 4 | — |
| C20-22 alcohols | 4.6 | — |
| Cetyl palmitate | 2 | — |
| Ceteareth-60 myristyl glycol | 0.01 | — |
| Mineral oil | 60 | — |
| Carbomer | 0.1 | 0.4 |
| EDTA | 0.2 | — |
| Ascorbic acid | 0.12 | 0.25 |
| Ammonium hydroxide | — | 4.57 |
| Pentasodium pentetate | — | 0.8 |
| Lauric acid | — | 3 |
| Polyquaternium-22 | — | 1.52 |
| Propylene glycol | — | 10 |
| Glycol distearate | — | 2 |
| Deceth-3 | — | 9 |
| Cetearyl alcohol | — | 11.5 |
| Hexadimethrine chloride | — | 3 |
| Laureth-12 | — | 7 |
| Oleth-30 | — | 4 |
| Silica dimethyl silylate | — | 1.2 |
| Titanium dioxide | — | 0.15 |
| Water | Qs 100 | Qs 100 |

Oxidizing Compositions (in g % of Active Material)

|  | B6 | B7 |
|---|---|---|
| Diethylenetriaminepentaacetic acid, pentasodium salt | 0.06 | 0.06 |
| Hydrogen peroxide | 6 | 6 |
| Disodium tin hexahydroxide | 0.04 | 0.04 |
| Tetrasodium pyrophosphate decahydrate | 0.03 | 0.02 |
| Liquid petroleum jelly | 20 | — |
| Poly[(dimethyliminio)-1,3-propanediyl(dimethyliminio)-1,6-hexanediyl dichloride] as an aqueous solution at 60% | 0.15 | — |
| Polydimethyldiallylammonium chloride | 0.2 | — |
| Glycerol | 0.5 | 0.5 |
| Cetylstearyl alcohol ($C_{16}/C_{18}$, 30/70) | 6 | 2.28 |
| Oxyethylenated stearyl alcohol (20 OE) | 5 | — |
| PEG-4 rapeseedamide | 1.2 | — |
| Vitamin D: DL-alpha-tocopherol | 0.1 | — |
| Trideceth-2 carboxamide MEA | — | 0.85 |
| Ceteareth-25 | — | 0.57 |
| Phosphoric acid | qs pH = 2.2 ± 0.2 | qs pH = 2.2 ± 0.2 |
| Water | qs 100 | qs 100 |

Composition A6 is mixed with the oxidizing composition B6 in a 1:1 weight ratio.

The dye composition A7 is mixed with the oxidizing composition B7 in a 1:1.5 weight ratio.

In each of the mixtures thus obtained, the concentration of base and 2-amino-5-ethylphenol.HCl coupler is $1.25 \times 10^{-3}$ mol per 100 g of mixture.

The mixtures thus obtained, A6+B6 and A7+B7, are applied to locks of natural hair containing 90% grey hairs.

After a leave-on time of 35 minutes at ambient temperature, the locks are rinsed with clear water, then washed with a shampoo. Finally, the locks are dried.

The colorimetric measurements are performed using a Minolta CM2006D spectrocolorimeter (illuminant D65, angle 10°, specular components included) in the CIELab system.

L* represents the lightness: the lower the value of L*, the more powerful the colouration obtained. C* represents chromaticity and is obtained via the equation:

$$C^* = (a^{*2}+b^{*2})^{1/2}$$

The higher the value of C*, the more chromatic the colouration obtained.

|  | L* | a* | b* | C* |
|---|---|---|---|---|
| A6 + B6 (invention) | 33.88 | 3.66 | 9.62 | 10.30 |
| A7 + B7 (comparative) | 36.96 | 2.54 | 4.89 | 5.56 |

The mixture A6+B6 according to the invention results in a more powerful and more chromatic colouration compared with the comparative mixture A7+137.

Example 4

The following dyeing compositions were prepared (in g % of active material unless otherwise mentioned)

|  | C (comparison) | A8 (invention) | A9 (invention) |
|---|---|---|---|
| Cetyl Stearyl alcohol [solid] | 15 | — | — |
| Glycerin mono stearate [solid] | 2.3 | — | — |
| Lanolin alcohol [solid] | 3.8 | — | — |
| Paraffine oil [liquid] | — | 21.1 | 53 |
| Sodium lauryl diglycol ether sulfate | 1 MA | 1 MA | 1 MA |
| Steareth-20 | 1.42 | 1.42 | 1.42 |
| Ethanol | 7.8 | 7.8 | 7.8 |
| Ascorbic acid | 0.3 | 0.3 | 0.3 |
| Sodium sulfite, anhydre | 0.3 | 0.3 | 0.3 |
| Ethylene diamine tetracetic acid, disodium salt hydrate | 0.3 | 0.3 | 0.3 |
| Ammonium hydroxide (22%) | 10 | 10 | 10 |
| Perfume | 0.2 | 0.2 | 0.2 |
| 1,4-diamino-2-methylbenzene sulfate | 2.5 | 2.5 | 2.5 |
| Resorcinol | 2.625 | 2.625 | 2.625 |
| 2-Amino-5-ethylphenol HCl | 1.673 | 1.673 | 1.673 |
| 1-hydroxyethyl-4,5-diamino pyrazole sulfate | 2.5 | 2.5 | 2.5 |
| 5-amino-2-methylphenol | 2.625 | 2.625 | 2.625 |
| water | Qs 100 | Qs 100 | Qs 100 |
| Amount of liquid fatty substance after mixing with hydrogen peroxide composition in a ratio 1.5 + 1 |  |  | 31.8% |

The composition C contains 21.1% of solid fatty substances. Composition A8 according to the invention contains 21.1% of liquid fatty substance and A9 contains 53% of liquid fatty substance.

At the time of use, the compositions C, A8 and A9 were mixed with a composition of hydrogen peroxide (30 Vol/9 g % of H2O2) in a ratio 1.5/1).

Each of the resulting mixture was applied on highly sensitized hair containing 90% of white hair (alcaline solubility=40). 10 g of the mixture were applied to 1 g of hair.

After 30 min at 40° C., the hair was rinsed, washed with a shampoo and then dried.

The colorimetric measurements are performed using a spectrocolorimeter SF600X Datacolor (illuminant D65, angle 10°, specular components included) in the CIELab system wherein L* represents the intensity of the coloration. The lower L* is, the more intense the color of the hair is.

The results are reported in the table below:

|  | L* Sensitized hair |
|---|---|
| Compositions obtained from C | 19.4 |
| Composition obtained from A8 (Inv) | 17.2 |
| Composition obtained from A9 (Inv) | 14.9 |

The compositions according to the invention obtained from A8 and A9 exhibit a L* value lower than the one obtained from the comparative composition C. This means that the intensity of the coloration obtained from the composition of the invention A8 and A9 is significantly higher than the one obtained from the comparative composition C.

Furthermore the mixture obtained from A9 exhibits a L* value lower than the one obtained from the composition A8, thus providing an even more intense coloration than the composition obtained from A8.

The invention claimed is:

1. A composition for dyeing keratin fibers, comprising:
   at least one oxidation base;
   at least one 2-amino-5-ethylphenol, a salt thereof, or a solvate thereof; and
   at least one liquid fatty substance different from salified fatty acids, present in an amount of at least about 35% by weight, relative to the total weight of the composition;
   wherein the composition is aqueous; and
   wherein the composition does not comprise a 3-aminopyrazolo[1,5-a]pyridine oxidation base or a derivative thereof.

2. The composition of claim 1, wherein the at least one liquid fatty substance is chosen from $C_6$ to $C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid fatty acid and/or fatty alcohol esters other than triglycerides, silicone oils, or mixtures thereof.

3. The composition of claim 1, wherein the at least one liquid fatty substance is chosen from liquid hydrocarbons comprising more than 16 carbon atoms.

4. The composition of claim 1, wherein the at least one liquid fatty substance is chosen from liquid petroleum jelly.

5. The composition of claim 1, wherein the at least one liquid fatty substance is present in an amount ranging from 35% to 55% by weight, relative to the total weight of the composition.

6. The composition of claim 1, wherein the at least one oxidation base is chosen from para-phenylenediamines, bis (phenyl)alkylenediamines, para-aminophenols, bis-para-aminophenols, ortho-aminophenols, heterocyclic bases, the salts thereof, or the solvates thereof.

7. The composition of claim 1, wherein the at least one oxidation base is chosen from heterocyclic bases, the salts thereof, or the solvates thereof.

8. The composition of claim 1, wherein the at least one oxidation base is chosen from 4,5-diamino-1-(β-hydroxyethyl)pyrazole, 2,3-diamino-6,7-dihydro-1H,5H-pyrazolo[1,2-a]pyrazol-1-one, 1-dimethylpiperazin-1-ium chloride, the salts thereof, the solvates thereof, or mixtures thereof.

9. The composition of claim 1, further comprising at least one additional coupler.

10. The composition of claim 9, wherein the at least one additional coupler is chosen from 6-hydroxybenzomorpholine, 2,4-diaminophenoxyethanol, 1,3-dihydroxybenzene, 1-hydroxy-3-aminobenzene, 2-methyl-5-hydroxyethylaminophenol, 2-methyl-1,3-dihydroxybenzene, 2-amino 3-hydroxypyridine, the salts thereof, the solvates thereof, or mixtures thereof.

11. The composition of claim 1, further comprising at least one surfactant.

12. The composition of claim 11, wherein the at least one surfactant is chosen from non-ionic surfactants.

13. The composition of claim 1, further comprising at least one alkaline agent.

14. The composition of claim 1, further comprising at least one chemical oxidizing agent.

15. The composition of claim 14, wherein the at least one chemical oxidizing agent is chosen from hydrogen peroxide.

16. The composition of claim 1, further comprising at least one alkaline agent and/or at least one chemical oxidizing agent, and wherein the at least one liquid fatty substance is present in an amount ranging from about 35% to about 55% by weight, relative to the total weight of the composition.

17. A method for dyeing keratin fibers, comprising applying to the keratin fibers a dye composition (A), the dye composition (A) comprising:
    at least one oxidation base;
    at least one 2-amino-5-ethylphenol, a salt thereof, or a solvate thereof; and
    at least one liquid fatty substance different from salified fatty acids, present in an amount of at least about 35% by weight, relative to the total weight of the composition;
    wherein the composition (A) is aqueous; and
    wherein the composition does not comprise a 3-aminopyrazolo[1,5-a]pyridine oxidation base or a derivative thereof.

18. The method of claim 17, further comprising mixing the dye composition (A) with an oxidizing composition (B), the oxidizing composition (B) comprising at least one chemical oxidizing agent.

19. The method of claim 18, wherein the total amount of fatty substances is greater than or equal to about 30% by weight, relative to the total weight of the composition resulting from the mixing of compositions (A)+(B).

20. A device for dyeing keratin fibers, the device comprising:
    at least one first compartment comprising a dye composition (A), the dye composition (A) comprising:
        at least one oxidation base;
        at least one 2-amino-5-ethylphenol, a salt thereof, or a solvate thereof; and
        at least one liquid fatty substance different from salified fatty acids, present in an amount of at least about 35% by weight, relative to the total weight of the composition;
        wherein the composition (A) is aqueous; and
        wherein the composition does not comprise a 3-aminopyrazolo[1,5-a]pyridine oxidation base or a derivative thereof; and
    at least one second compartment comprising an oxidizing composition (B) comprising at least one chemical oxidizing agent.

* * * * *